(12) United States Patent
Liles et al.

(10) Patent No.: US 6,248,567 B1
(45) Date of Patent: Jun. 19, 2001

(54) TEMPLATE-SPECIFIC TERMINATION IN A POLYMERASE CHAIN REACTION

(75) Inventors: Mark R. Liles; Robert M. Goodman, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/557,248

(22) Filed: Apr. 24, 2000

(51) Int. Cl.[7] .................................................. C12P 19/34
(52) U.S. Cl. ........................ 435/91.1; 435/91.1; 435/91.2; 435/6; 435/7.1; 435/15; 536/24.2; 536/243; 935/77; 935/78
(58) Field of Search .................... 435/91.1, 91.2, 435/6, 7.1, 15; 536/24.2, 24.3; 935/77, 78

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 5,213,961 | 5/1993 | Bunn et al. . |
| 5,219,727 | 6/1993 | Wang et al. . |
| 5,747,251 | 5/1998 | Carson et al. . |
| 5,759,822 | 6/1998 | Chenchik et al. . |

OTHER PUBLICATIONS

Li, H.; Gyllensten, U.B.; Cui, X.; Saiki, R.K.; Erlich, H.A.; Arnheim, N.; Amplification and analysis of DNA sequences in single human sperm and diploid cells, *Nature*, 1988, 335:414–417.

*Primary Examiner*—W. Gary Jones
*Assistant Examiner*—Janell E. Taylor
(74) *Attorney, Agent, or Firm*—Joseph T. Leone, Esq.; DeWitt Ross & Stevens S.C.

(57) ABSTRACT

Described herein is a method for selectively inhibiting the amplification of a specific DNA template during a polymerase chain reaction (PCR). In particular, the method is useful when the sequences of the desired and undesired DNA templates are similar. A set of universal primers binds to both the desired and undesired DNA templates during a PCR, resulting in the amplification of their DNA sequences. The method targets the undesired DNA template with three sets of oligonucleotide primers, one set of which is terminally modified to both prevent primer extension and increase the primer-template binding affinity. The result of these terminal modifications is the specific inhibition of the PCR amplification of the undesired DNA template, allowing the preferential amplification of the desired DNA templates.

22 Claims, 9 Drawing Sheets

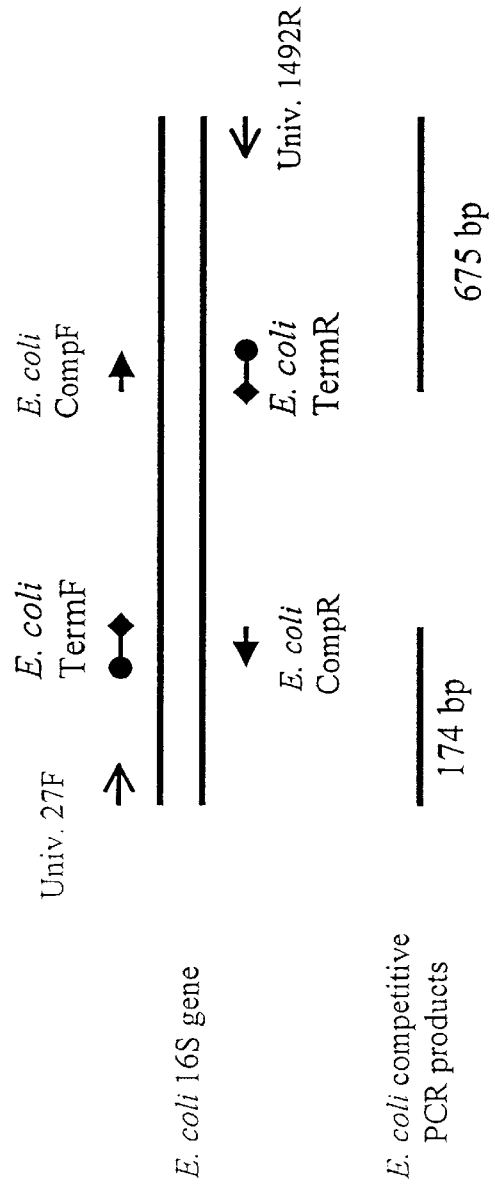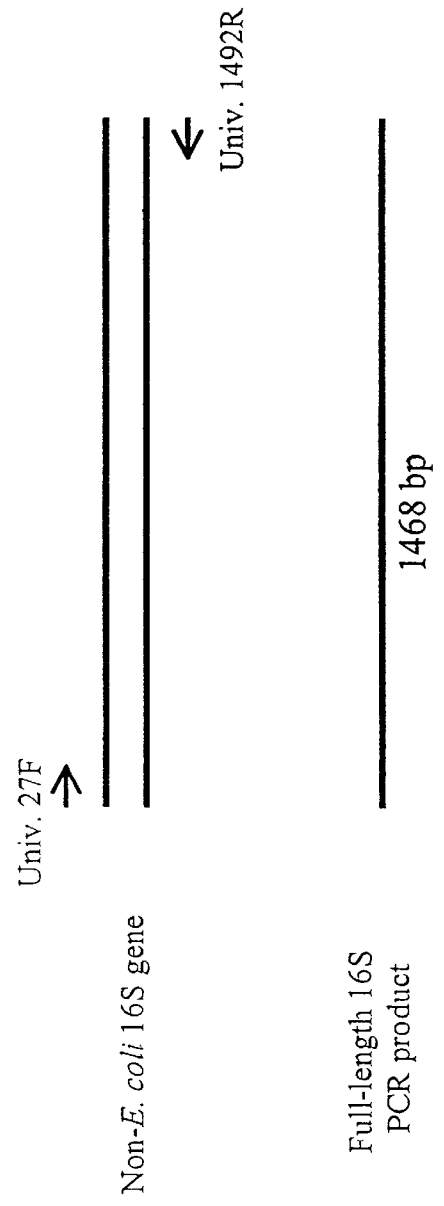
FIG. 3A
FIG. 3B

TEMPLATE-SPECIFIC TERMINATION IN A POLYMERASE CHAIN REACTION

REFERENCE TO GOVERNMENT GRANT

This invention was made with United States Government support awarded by NIH Grant # AI42786. The United States Government has certain rights in this invention.

FIELD OF THE INVENTION

The invention is generally directed to molecular biology techniques. Specifically, the invention is related to a method for selectively amplifying nucleic acids.

DESCRIPTION OF THE RELATED ART

The polymerase chain reaction (PCR) is a powerful tool with which nucleic acids (typically DNA) can be exponentially amplified. The basic PCR techniques are described in U.S. Pat. Nos. 4,683,195 and 4,683,202 to Mullis, et al. PCR is run in cycles, typically with three different temperatures: denaturation, annealing, and extension. Two-temperature PCR is also possible. At the denaturation temperature, DNA templates are denatured. At the annealing temperature, primers anneal to the DNA template. PCR uses a thermally stable polymerase and at least one set of primers (i.e., two primers), which are short pieces of DNA typically around 20 base pairs, and which are present in a quantity in excess of the template. At the extension temperature, the polymerase extends the primers to form new DNA molecules. Primers and the extension products (i.e., the PCR products) are then melted from the target DNA, and a new cycle of PCR can commence with both the original target and the newly synthesized PCR products serving as templates in the next cycle of PCR. Hence, the exponential amplification.

In general, primers are designed based on known template sequences. One primer primes the sense strand, and the other primes the complementary strand of the target DNA. PCR can be performed on a uniform target DNA (i.e., targets with the same sequence) or on mixed target DNAs, (i.e., targets with different intervening sequences flanked by conserved sequences). For mixed target DNAs, even mismatched primers function in the PCR if the sequence of the targets have enough complementarity to the mismatched primers.

PCR is such a powerful tool that even a single molecule of template can be amplified. Li, H. et al. (1988) Nature 335:414–417. Although it has been possible to amplify large amounts of a rare template, it has been more difficult to amplify rare templates when they are mixed with similar templates, especially when rare templates are mixed with similar templates that are much more abundant.

Thus a need still exists for a method that amplifies desired templates while excluding or preventing amplification of similar undesired templates. One further challenge to amplifying only desired DNA templates in a mixed population is that in some mixed populations, one population member is often over-represented. Thus, amplification of the templates of interest results in an over-abundance of the one population member and a dearth of amplification of other species, including novel species.

When first practiced, PCR was not a quantitative method. That is, the number of PCR products generated was not representative of the initial starting number of template DNA molecules. This is due to several factors including (1) amplification is exponential, (2) a plateau effect, (3) substrate depletion, and (4) a preference to amplify small DNA targets over large DNA targets. Several modifications have been made to the PCR to make the technique quantitative. See, for example, U.S. Pat. No. 5,213,961 to Bunn, et al., which describes a process for quantitating nucleic acid species in a sample; and U.S. Pat. No. 5,219,727 to Wang, et al., which describes a method for determining the amount of a template nucleic segment in a sample by polymerase chain reaction.

Quantitative PCR is a powerful tool when the goal is to quantitate template DNAs. However, quantitative PCR is not useful if the goal is to amplify only certain desired DNA templates in a mixed population of templates. Sequence-specific PCR (or allele-specific PCR), can be used when the majority (or all) of the potential DNAs are known. Sequence-specific primers can be designed to bind to and amplify only certain target DNAs. However, when the majority (or all) of the potential DNAs are not known, this technique cannot be used.

It is useful then to devise a way to inhibit amplification of certain population members, especially without sorting a sample before amplification. It is desirable to amplify some nucleic acids while, at the same time, inhibiting the amplification of other nucleic acids. Some methods have been developed to address this goal. For example, U.S. Pat. No. 5,759,822 to Chenchik, et al. describes a method for adapter-mediated suppression of PCR amplification, in which adapters are ligated to DNA fragments. The adapters on either end (i.e., terminus) of the fragment can anneal to each other to form suppressive "pan-like" double-stranded structures that suppress amplification of the fragments during PCR. This method, however, is useful only for small fragments of DNA with known terminal sequences, such as cDNA/mRNA hybrid molecules and restriction fragments.

However, none of the above-noted approaches yields a method that can exclude at least some of undesired DNA templates from amplification and, at the same time, amplify desired DNA templates which are related to the undesired DNA templates. Such a method, described herein, expands the applicability of PCR methods to include mixed DNA templates having desired and undesired DNA templates, even when the desired DNA templates are unknown.

SUMMARY OF THE INVENTION

Described herein is a method for selectively amplifying a desired DNA template in samples containing a mixture of undesired and desired DNA templates. The method amplifies desired DNA templates and inhibits the amplification of the undesired DNA templates. In particular, the method is useful when some of the desired DNA templates have unknown intervening sequences and when the sequences of the desired and undesired DNA templates are similar. In the development of this technology, two primer sets were used: a first primer set that is a universal primer set and a second primer set that is a competitor primer set. Each primer set has a forward and a reverse primer. The forward primers of both the universal and competitor primer sets bind to the same strand. The competitor primer set binds to the undesired DNA template and inhibits the amplification of the undesired DNA template and generates a smaller PCR product from the undesired DNA template, allowing a larger PCR product to be generated from the desired DNA template. This method for competitively inhibiting amplification of an undesired DNA template has been described in the art. However, the problem with the use of competitor primers to generate smaller, undesired DNA template-specific PCR products is that the energy in the PCR is directed towards amplifying the smaller, competitive PCR products (i.e., the undesired fragments) instead of the desired DNA template.

In the preferred embodiment, three primer sets are used: a universal primer set, a competitor primer set, and a terminator primer set. This embodiment results in the inhibition of undesired DNA template amplification without significant generation of competitive PCR products, allowing PCR amplification from the desired DNA template. Preferably, the terminator primers have modifications at the 5' and 3' ends of the DNA sequence. Preferably, the 5' modification increases the primer-DNA template binding affinity and prevents the terminator primer from being displaced after it hybridizes to a DNA template. Preferably, the 3' modification inhibits primer extension, thereby preventing the generation of a PCR product from the terminator primer. The 5' and 3' modifications result in terminator primers with exceptionally high affinity for the undesired DNA template. The terminator primers bind to the undesired DNA template at much higher temperatures than the universal primers and directly interfere with the PCR amplification of the undesired DNA template by the universal primers. The sequence of each terminator primer is both identical to a region of the undesired DNA template that is not in common with the desired DNA templates and is complementary to the sequence of the opposite competitor primer (e.g., the forward terminator primer sequence is complementary to the reverse competitor primer sequence). The combination of competitive and terminator primer sets results in the improved inhibition of the undesired DNA template while increasing the PCR amplification of the desired DNA template.

In short, the invention is directed to a method of selective amplification having the following steps: providing a first primer set that binds to both the desired nucleic acid and undesired nucleic acid present in a sample of nucleic acid to be amplified; providing a second primer set that binds to the undesired nucleic acid, wherein the second primer set inhibits the amplification of the undesired nucleic acid by the first primer set; providing a third primer set that binds to the undesired nucleic acid, wherein, when compared to the second set, the third primer set further inhibits the amplification of the undesired nucleic acid by the first primer set; and amplifying the desired nucleic acid with the first primer set.

The invention is also directed to a method for selectively amplifying a desired nucleic acid including the following steps: providing a first primer set that binds to both a desired nucleic acid and the undesired nucleic acid present in a sample of nucleic acid to be amplified, wherein the first primer set comprises a forward primer and a reverse primer; providing a second primer set that binds to the undesired nucleic acid, wherein (i) the second primer set at least partially inhibits the amplification of the undesired nucleic acid by the first primer set, wherein the second primer set comprises a forward primer and a reverse primer and (ii) the forward primer of both the first and second primer sets binds to the same strand of the undesired nucleic acid, and the reverse primer of both the first and second primer sets binds to the same strand of the undesired nucleic acid; providing a third primer set that blocks the amplification of the undesired nucleic acid with the first primer set, wherein (i) the third primer set comprises a forward primer and a reverse primer, the third primer set binds to the undesired nucleic acid and at least partially inhibits the amplification of the undesired nucleic acid by the first primer set, the forward primer of the third primer set binds to the opposite strand of the undesired nucleic acid as the forward primers of the universal and competitor primer sets, and the reverse primer of the third primer set binds to the opposite strand of the undesired nucleic acid as the reverse primer of the universal and competitor primer sets, (iv) the forward primer and reverse primer of the third primer set are each modified at their 3' and 5' termini, (v) the 5' modification increases primer-DNA affinity and prevents displacement of the third primer set, and (vi) the 3' modification prevents primer extension; and amplifying the desired nucleic acid with the first primer set, wherein the desired nucleic acid is amplified with a polymerase chain reaction.

It is a principal aim of the invention to provide a method to inhibit amplification of undesired DNAs and to allow simultaneously for the amplification of similar, desired DNAs in a sample that is a mixture of the undesired and desired DNAs.

A further aim of the present invention is to amplify desired DNA when the sequence of the desired DNA is unknown. It is also an aim of the invention to amplify selectively mixtures of phylogenetically related desired and undesired DNAs. The selective PCR amplifies the desired DNAs and simultaneously inhibits the amplification of at least some, and preferably most or all, of the undesired DNAs.

A further aim of the present invention is to selectively amplify DNA templates that are cloned into a host organism wherein the host organism also contains a sequence related to the cloned DNA.

A further aim of the invention is to provide a method to amplify selectively forensic samples, maternal/fetal samples, 16S rRNA libraries, other libraries, and other diagnostics. Another aim of the invention is to provide a method for selective amplification of desired DNA during in situ PCR.

Further aims, objects, and advantages of the methodology described herein will become apparent upon a complete reading of the Detailed Description which follows.

BRIEF DESCRIPTION OF THE DRAWINGS

FIG. 1A shows the binding of the universal and competitor primer sets to the *E. Coli* 16S gene. FIG. 1B depicts the binding of these primer sets to non-*E. Coli* 16S genes.

FIGS. 3A and 3B are schematic diagrams of a preferred embodiment of the invention in which three primer sets are employed. FIG. 3A shows the binding of the universal and competitor primer sets to the *E. Coli* 16S gene. FIG. 3B depicts the binding of these primer sets to non-*E. Coli* 16S genes.

DEFINITIONS

Figure 1:
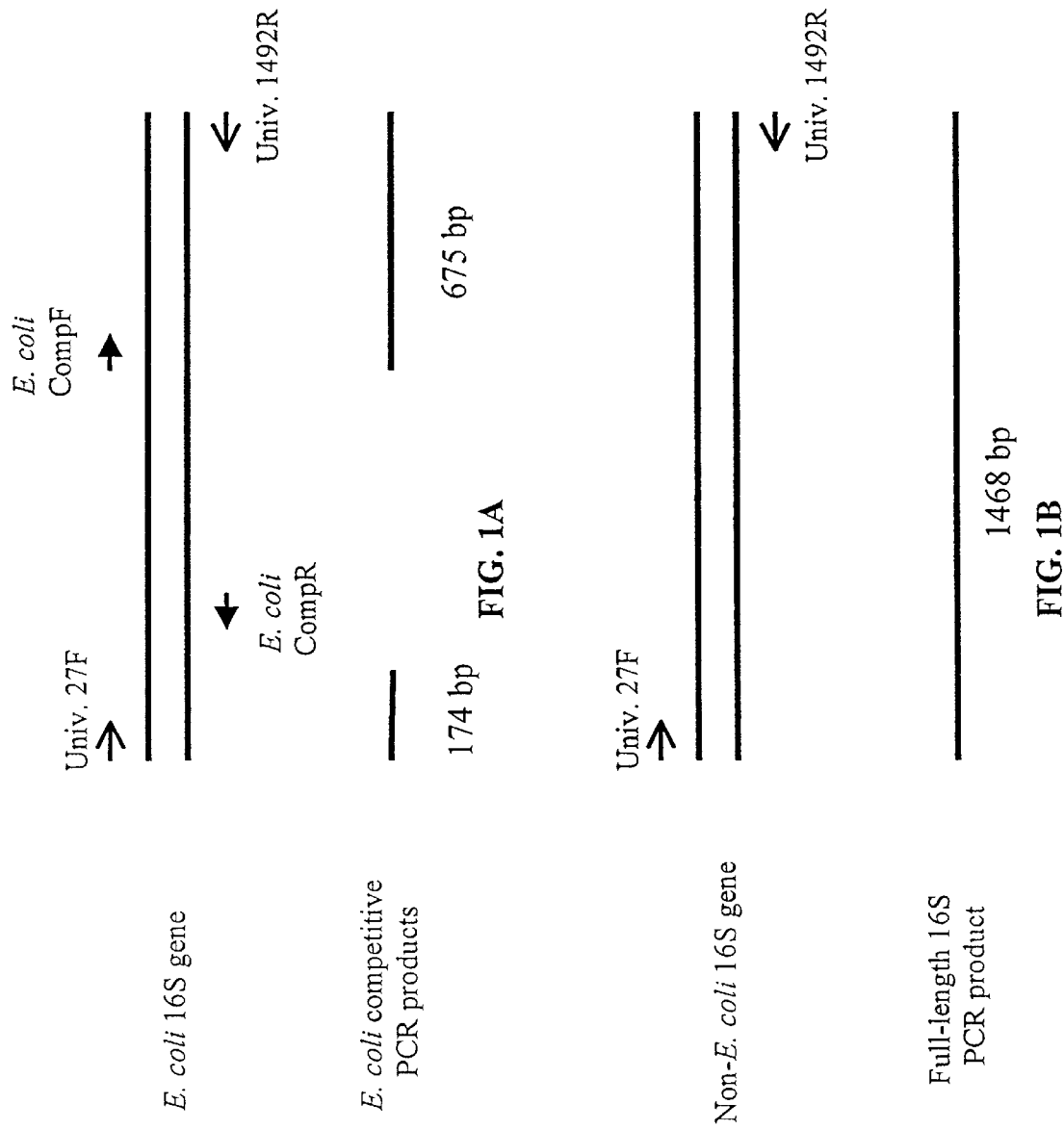
FIGS. 1A and 1B are schematic diagrams of a first preferred embodiment of the invention in which two primer sets are employed.

Competitor Primers: a primer set that binds to the undesired DNA, which at least partially (and preferably substantially completely) inhibits the amplification of the undesired DNA by the universal primer set.

Desired DNA: "undesired" and "desired" refer to the goal of the amplification-in short, desired DNA is the DNA the researcher is interested in examining in isolation from other, potentially related DNA present in a sample. For example, using the present invention, a desired "gene X" from organism A can be selectively amplified from a mixture of DNA containing the desired "gene X" from organism A, as well as large amounts of related "gene X'" DNA from distinct organisms B, C, and D. It should be noted that the subject invention is exemplified with DNA; however, the subject invention is applicable to other nucleic acids, such as mRNA and cDNA with the appropriate modifications known in the art.

Mixed target DNA: multiple DNA sequences in a single reaction that can all be PCR amplified with a set of universal primers, but vary in the regions between the primer sites, producing a heterogeneous mixture of PCR products.

Polymerase chain reaction (PCR): a technique in which cycles of denaturation of a nucleic acid template, annealing with primer, and extension with DNA polymerase are used to amplify the number of copies of a target DNA sequence by $10^6$ or more times. The PCR process for amplifying nucleic acids is covered by U.S. Pat. Nos. 4,683,195, and 4,683,202, which are incorporated herein by reference for a description of the process.

Primer: a single-stranded oligonucleotide or DNA fragment that is designed to hybridize (i.e., bind specifically) to the opposing strand of a target DNA.

Primer set: two primers including primer 1 that hybridizes to a single strand at one end of the DNA sequence to be amplified and primer 2 that hybridizes with the other end on the complementary strand of the DNA sequence to be amplified. Also referred to as the forward (F) and reverse (R) primers.

Primer site: the area of the template DNA to which a primer hybridizes.

Template DNA: a DNA sequence that hybridizes to primers and is amplified during a PCR. The template DNA can be either a uniform template DNA or a mixed template DNA as defined in this section.

Terminator Primers: a primer set that binds to the undesired template DNA, inhibiting the PCR amplification of the undesired DNA template by the universal primer set. Preferably, the terminator primer set has both 5' and 3' modifications. It is also preferred that the terminator primers are the reverse complement sequence of the competitor primer set.

Undesired DNA: Refer to "Desired DNA. " The term undesired DNA is this context only refers to DNA sequences with significant homology to the desired DNA, and not DNA sequences, also undesirable to be PCR amplified, that may also be present in the PCR but do not share homology with the target DNA and therefore will not be PCR amplified with the universal primers.

Uniform template DNA: a single DNA sequence that can be PCR amplified with a set of universal primers, producing PCR products that are all identical.

Universal Primers: a primer set that binds to both the desired DNA and the undesired DNA, and which can amplify both the desired DNA and the undesired DNA in the absence of the competitor or terminator primer sets. In the presence of the competitor and terminator primer sets, the desired DNA is amplified by the universal primer set, and amplification of the undesired DNA by the universal primer set is inhibited.

DETAILED DESCRIPTION OF THE INVENTION

The present invention provides a method for the selective amplification of DNA molecules containing a mixture of undesired DNAs and desired DNAs. The terms undesired and desired refer to the goal of the amplification. For example, to amplify genes $X_A$, $X_B$, and $X_C$, derived from the organisms A, B, and C, respectively, from a mixed target DNA containing genes $X_A$, $X_B$, $X_C$, and $X_D$, where $X_D$ is from organism D, then the genes $X_A$, $X_B$, and $X_C$, are the desired DNA templates and gene $X_D$ is the undesired DNA template.

In the specific case illustrated below, gene X is the gene that encodes the small subunit 16S ribosomal RNA, denoted as 16S rRNA, the sequence of which is used for deducing the identity and evolutionary history of all life forms. Genes $X_A$, $X_B$, and $X_C$ represent the 16S rRNA genes of environmental organisms A, B, and C, the partial genomes of which are present in a genomic library contained within a host *Escherichia coli*. The host *E. coli* genome also contains several copies of the native *E. coli* 16S rRNA gene (i.e., $X_D$ in the previous example). Therefore, to identify the environmental organisms represented in the genomic library, it became necessary to devise a method to identify the non-host 16S rRNA genes present in the library, while inhibiting the amplification of the native *E. coli* 16S rRNA genes. In particular, the present invention provides a method which is especially useful when the sequences of the desired and undesired DNA templates are similar, or contain short regions of conserved DNA sequence, as is the case for the 16S rRNA genes. Furthermore, the desired DNA templates can include both known and unknown sequences, making this technology useful for a wide variety of applications.

Template-specific termination in a PCR is also useful for amplifying genes present in genomic libraries constructed from a variety of environmental sources, such as insect intestines, plant rhizospheres, microbial mats, sulfur springs, ocean and fresh water ecosystems, and extremeophilic organisms found in the harsh environments surrounding thermal vents, geysers, and the like. In addition to the 16S rRNA genes present in these environmental genomic libraries, there are other genes of interest that can be selectively PCR amplified using this technology. This technique is also useful for in situ PCR, screening other genomic libraries constructed from specific organisms, and for diagnostic purposes.

The subject method can be practiced when at least the complete sequence of one DNA in a mixed template PCR is known. For example, in a forensic sample, the victim's DNA sequence of interest is determined and subsequently inhibited during the amplification of a mixed target DNA sample containing both victim DNA (undesired DNA) and perpetrator DNA (desired DNA). Similarly, in a maternal/fetal sample, the maternal DNA sequence is determined and subsequently inhibited during the amplification of a mixed target DNA sample containing both the maternal DNA (undesired) and fetal DNA (desired).

PCR amplifications typically include a buffer, primers, templates, and a polymerase. The buffer is typically 10 mM Tris, pH 8.3, 50 mM KCl, 1.5 mM $MgCl_2$, 0.1% gelatin. The $MgCl_2$ concentration in the final reaction mixture is usually between 0.5 and 5.0 mM. The optimum $MgCl_2$ concentration is determined empirically. Primers, typically 20–30 nucleotides in length, are included in the PCR reaction. Primers bind to template DNA and amplify the region between the two primers. The $T_m$ of primer hybridization can be calculated using various formulas. The most common formula is: $T_m$={(number of A+T residues)×2° C.}+{(number of C+G residues)×4° C.}. Primer concentrations are calculated based on the absorbance of the primer at 260 nm. A 1.0 molar solution of dT has a value of 8,400 absorbance units at 260 nm; a 1.0 molar solution of dA has a value of 15,200 absorbance units at 260 nm; a 1.0 molar solution of dG has a value of 12,010 absorbance units at 260 nm; and a 1.0 molar solution of dC has a value of 7,050 absorbance units at 260 nm. For example, a 1 M primer solution of '5-TAGC- 3' would have a molar extinction coefficient of 42,660 at 260 nm. Likewise, a 10 micromolar solution of this primer would give an absorbance of 0.427 at 260 nm.

Initially PCR starts out at a high temperature (the denaturation temperature) at which template DNA (typically double-stranded DNA) is denatured. The temperature then is decreased to a low temperature (annealing temperature) at which the primers bind the target DNA. The temperature is then increased to an intermediate temperature (the extension temperature) between the annealing temperature and the denaturation temperature at which the polymerase extends the primers. The whole process is then repeated 20 to 40 times, resulting in an exponential increase in the number of copies of the DNA template with each cycle. The power of PCR to amplify even a single copy of a template over a million-fold within a few hours explains its value in molecular biology. But the exponential amplification of a DNA target is also a severe weakness if a particular template swamps the production of other, similar templates that are desired. Thus, the need for template-specific inhibition in a PCR.

Many of the steps noted below for the manipulation of DNA, including digesting with restriction endonucleases, amplifying by PCR, separating DNA by gel electrophoresis, and the like, are well known and widely practiced by those skilled in the art and are not extensively elaborated upon herein. Unless otherwise noted, the DNA protocols utilized herein are described extensively in Sambrook, J., E. F. Fritsch, and T. Maniatis, (1989), "Molecular Cloning: A Laboratory Manual," Cold Spring Harbor Laboratory Press: New York, N.Y.

The first attempt at preventing the PCR amplification of the undesired E. coli 16S rRNA gene utilized a competitive strategy as diagramed in FIGS. 1A and 1B. In this strategy, two primer sets were employed, both of which would bind to the E. coli 16S rRNA gene, generating two PCR products (FIG. 1A). The two competitor primers, designated CompF and CompR, were designed to hybridize to a variable region of the 16S rRNA gene, based upon the sequence of all known organisms present in the GenBANK database. The sequence of the forward competitor primer (CompF) in this instance was 5'-GAT GTC GAC TTG GAG GTT GTG CCC-3' (SEQ. ID. NO. 1), which hybridizes to the E. coli 16S gene at bp 817 (5'→3'). The sequence of the reverse competitor primer (CompR) was 5'-CCG ATG GCA AGA GGC CCG AAG GTC CCC C-3' (SEQ. ID. NO 2), which hybridizes to the E. coli 16S rRNA gene at bp 200 (3'→5').

The reverse competitor primer is specific to the genus Escherichia, whereas the forward competitor primer is specific to the genera Eschetichia, Salmonella, and Yersinia. Because none of the 16S rRNA genes from these bacteria were sought from the genomic library, the competitive inhibition of 16S rRNA genes from organisms closely related to E. coli was not a problem. This does illustrate, however, the advantage of having a large database of DNA sequences from which to develop the sequence of competitor primers.

The PCR amplification of all 16S rRNA genes is accomplished by the use of universal primers that are targeted to regions of the 16S gene found in every known bacteria (FIGS. 1A and 1B). For this study, the universal primers used were the forward primer Univ. 27F (5'-AGA GTT TGA TCM TGG CTC AG-3', where M is an A or C; SEQ. ID. NO. 3) and the reverse primer Univ. 1492R (5'-GGY TAC CTT GTT ACG ACT T-3', where Y is a C or a T; SEQ. ID. NO. 4)), both of which have been well characterized in the literature. According to the competitor strategy, the universal primers will bind to every 16S gene present in the mixed DNA template, including that of the E. coli host, which is well known to contaminate every preparation of genomic library DNA. Only the non-E. coli 16S genes will generate a full-length 1.5 kb PCR product in this strategy (FIG. 1B), due to the production of the two smaller, E. coli-specific, competitive PCR products (FIG. 1A).

Figure 2:
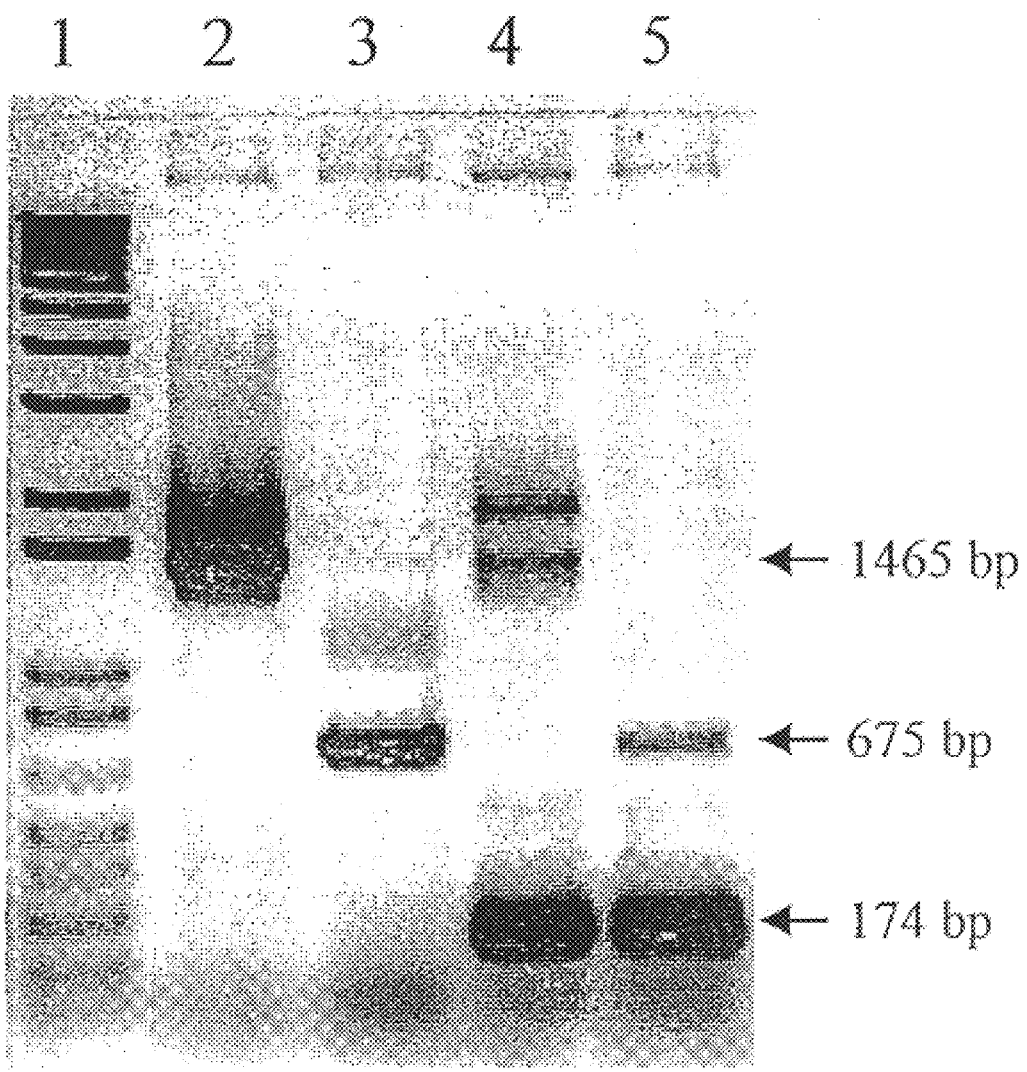
FIG. 2 is a photograph of an electrophoresis gel depicting a PCR with both the universal and competitor primer sets.

The competitive PCR strategy resulted in the appearance of the correctly-sized PCR products, but the vast majority of the reaction went into the production of the two smaller, E. coli-specific PCR products (see FIG. 2). To determine the inhibition effect of the competitor primers on amplification of E. coli genomic DNA by the universal primer set, the competitor primers were added both individually and as a pair to a PCR reaction having the universal primer set. The addition of the CompR primer to a PCR reaction having the universal primer set generates a 174 bp PCR product, which results from the CompR single-stranded amplification products being primed by the Univ. 27F primer. The addition of the CompF primer to a PCR reaction having the universal primer set generates a 675 bp PCR product, which results from amplification primed by the CompF primer and the Univ. 1492R primer. When the competitor primer set is used as a pair and is added to the universal primer set, PCR products of 174 and 675 bp are formed. The PCR reactions were set up as shown in Table 1:

TABLE 1

PCR Products of FIG. 2

| lane | template | primer set |
| --- | --- | --- |
| 1 | 1 KB PLUS Marker (Gibco-BRL) | |
| 2 | E. coli genomic DNA | U primer set |
| 3 | E. coli genomic DNA | U primer set, 10 nM CompF |
| 4 | E. coli genomic DNA | U primer set, 10 nM CompR |
| 5 | E. coli genomic DNA | U primer set, 10 nM CompF and CompR |

The amplification products from these reactions were subjected to gel electrophoresis, the results of which are shown in the gel of FIG. 2, the lane numbers of which correspond to the numbers in Table 1. In FIG. 2, the PCR product greater than 1500 bp seen in Lanes 2 and 4 is a non-specific PCR product that was not observed when the annealing temperature was increased (data not shown), and was similarly inhibited by the competitor primers.

Individually, the competitor primers reduced the PCR amplification of the E. coli 16S rRNA gene (FIG. 2, lanes 3 and 4), but only in combination with each other did these competitor primers completely inhibit the generation of a full-length (i.e., 1465 bp) PCR product (lane 5). This test of the competitor primers was judged a success because a full-length *E. coli* PCR product was not produced and two smaller products of the expected sizes appeared only when competitor primers were added to the reaction.

However, the amount of PCR product generated from the use of CompR (FIG. 2, lanes 4 and 5) is considerable, as would be expected because it is well established that PCR amplification of smaller DNA products results in much greater yields compared to larger DNA products. The competitor primers were also tested in controlled situations where non-*E. coli* 16S rRNA genes were known to be present in a mixed template DNA sample (data not shown). From these experiments it was very clear that the competitor primers biased the reaction in favor of the production of the smaller, *E. coli*-specific PCR products, yielding very little, if any, of the full-length PCR product. This result necessitated the search for alternative technologies for template-specific termination in a PCR.

Terminator oligos:

Because the competitor strategy did not yield the desired results (i.e., production of abundant non-*E. coli* PCR products), an alternative technology was sought. The competitor primers were modified to prevent the generation of an *E. coli*-specific PCR product, thereby conserving the energy of the PCR for the amplification of non-*E. coli* 16S genes. The prior art is silent regarding primer modifications that result in inhibiting the amplification of a specific template in a PCR. Therefore, primers were designed with terminal modifications to yield primers that 1) bind to the undesired DNA template; 2) do not produce a PCR product; and 3) interfere with the generation of other PCRs product from the undesired template.

The first primer modification tested was the addition of a phosphoramidite group to the 3' end of each competitor primer discussed above. It has been established in the literature that 3' phosphoramidite groups prevent the extension of DNA templates by Taq DNA polymerase, thereby preventing a PCR product being produced from either of the competitor primers.

Preferably, the 3' modification is a phosphoramidite, such as 3-(4,4'-dimethoxyltrityloxy)propyl-1-{ (2-cyanoethyl)-(N,N-diisopropyl)} -phosphoramidite.

A host of related phosphoramidites are also known and can function as the 3' modification. Examples include 2-{2-(4,4'-dimethoxytrityloxy)-ethylsulfonyl}ethyl-(2-cyanoethyl)-(N,N,-diisopropyl)-phosphoramidite):

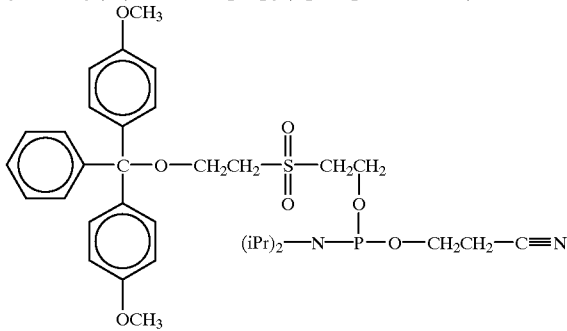

and 3-{(4,4'-Dimethoxytrityloxy)-2,2-dicarboxyethyl}propyl-(2-cyanoethyl)- (N,N-diisopropyl)-phosphoramidite:

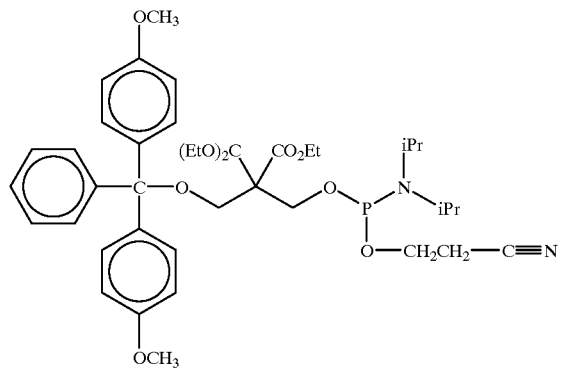

Any other 3' modification known to the art can also be used. For example, adding a phosphate group, a phosphate ester, or using an inverted 3'-3' linkage at the 3' hydroxyl group of the primer can be used to block extension at the 3' terminus. Another method of blocking the 3' terminus is to use a 2',3' dideoxynucleoside support. However, this is available for a limited number of bases.

In situations where it is necessary to have a selection of all of the bases available, it is possible to use 3'-deoxynucleoside supports as 3' terminators. Although the 2' hydroxyl group is still present in the final oligonucleotides, it is not a substrate for the routinely used polymerases.

Other potential blockers linked to supports include 5'-dimethoxytrityl-N-succinoyl-CPG (CPG=controlled-pore glass):

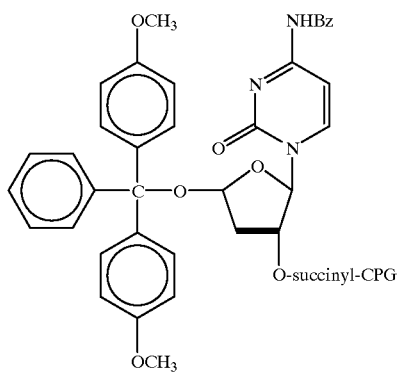

and 5'-dimethoxytrityl-N-benzoyl-3'-deoxycytosine, 2'-succinoyl-linker-CPG:

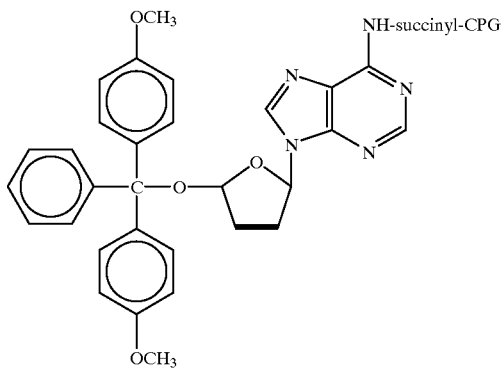

In the absence of complete inhibition of the amplification of undesired DNAs by the competitor primers, the competitor primers generate short PCR products (specific to the undesired DNA) by extending the competitor primer in one PCR cycle. In the next PCR cycle, that extension product can be primed by the universal primer. The competitor PCR products are shown in FIGS. 1A,1B, 3A, and 3B.

To test the effectiveness of the 3' phosphoramidite modification in preventing the amplification of the *E. coli* 16S rRNA gene, PCR was conducted as before (see Table 1 and FIG. 2) with the addition of the 3'-modified competitor primers. As expected, no small, *E. coli*-specific PCR product (i.e., 174 or 675 bp DNA, respectively) was detected, demonstrating the effectiveness of the 3' phosphoramidite group at preventing the competitor primers from producing PCR products (data not shown). However, a full-length, 1.5 kb PCR product was produced when the concentration of 3'-modified competitor primers was 1 μM, 10 μM, 100 μM, or even 1 mM (data not shown). This result suggested that the 3'-modified competitor primers did not interfere with the PCR from the universal primer sites. In other words, as the Taq polymerase extended the DNA strand from the universal primer sites, it removed the competitor primer(s) from this strand. This phenomenon is known as strand displacement activity, an activity possessed by many DNA polymerases, including Taq polymerases. This activity was not anticipated. The ability of the non-modified competitor primers to prevent the formation of the full-length *E. coli* PCR product was, therefore, due to the preferential formation of the smaller PCR products. Preventing the formation of the smaller PCR products by the 3' phosphoramidite modification thereby completely eradicated the template-specific inhibition of the competitor primers.

What was needed, therefore, was a way to prevent the Taq polymerase from displacing the competitor primers from the undesired DNA template (i.e., the *E. coli* 16S rRNA gene). The approach taken to solve this problem was to increase the stability of the competitor primers when bound to the undesired DNA template, thereby preventing Taq polymerase from displacing the competitor primers as it extended the DNA strand from the universal primer sites. Because there are many chemical compounds known to intercalate into a double-stranded DNA helix, these were the best candidates to increase the stability of the competitor primer/template interaction. The first DNA-intercalating compound tested was an acridine group, snythesized as a 5' modification of the competitor primers discussed above. Alternative DNA-intercalating compounds such as ethidium or others known in the art could also be employed instead of acridine, or a non-intercalating molecule, such as a biotin molecule, could be added to the 5' primer end. Because it was still necessary to prevent primer extension, a 3' phosphoramidite group was also added to each primer. Competitor primers with both 5'-acridine groups and 3'-phosphoramidite groups are hereafter referred to as terminator oligos. The sequence of each terminator oligo was complementary to that of a competitor primer, thereby bringing these terminator oligos closer to the universal primer sites on each DNA strand (FIGS. 3A and 3B). The sequence of the forward terminator primer (TermF) was 5'-GGG GGA CCT TCG GGC CTC TTG CCA TCG G-3' (SEQ. ID. NO. 5). The sequence of the reverse terminator primer (TermR) was 5'-GGG CAC AAC CTC CAA GTC GAC ATC-3'(SEQ. ID. NO. 6).

FIGS. 3A and 3B illustrate a preferred embodiment of the invention. Three primer sets are employed: a universal set, a competitor set, and a terminator set. FIG. 3A illustrates the three primer sets being used with the undesired *E. coli* template. FIG. 3B shows the three primer sets being used with the desired non-*E. coli* template. The first primer set is the universal primer set (the 3' end of which is designated ">" in FIGS. 3A and 3B) as described above. The second primer set (the 3' end of which is designated "◄")is the competitor primer set as described above. The third primer set is a terminator primer set (the 3' end of which is designated "♦" and the 5' end of which is designated "●"). The terminator primers preferably have both a 3' modification and a 5' modification. The two modifications to the terminator primer make it a preferred terminator primer. Preferably, the 3' modification is a 3' phosphoramidite and the 5' modification is an acridine group. The 5' modification increases the primer-DNA template binding affinity and prevents the displacement of the primer from the target DNA; the 3' modification prevents primer extension.

To test the ability of the terminator oligos to inhibit the PCR amplification of the *E. coli* 16S rRNA gene, reactions were carried out as before using *E. coli* genomic DNA and the universal primer set, with and without the addition of the competitor primers and/or terminator oligos. Table 2 lists the PCRs that were run initially to test the terminator oligos. The resulting PCR products are shown in FIG. 4.

TABLE 2

Figure 4:
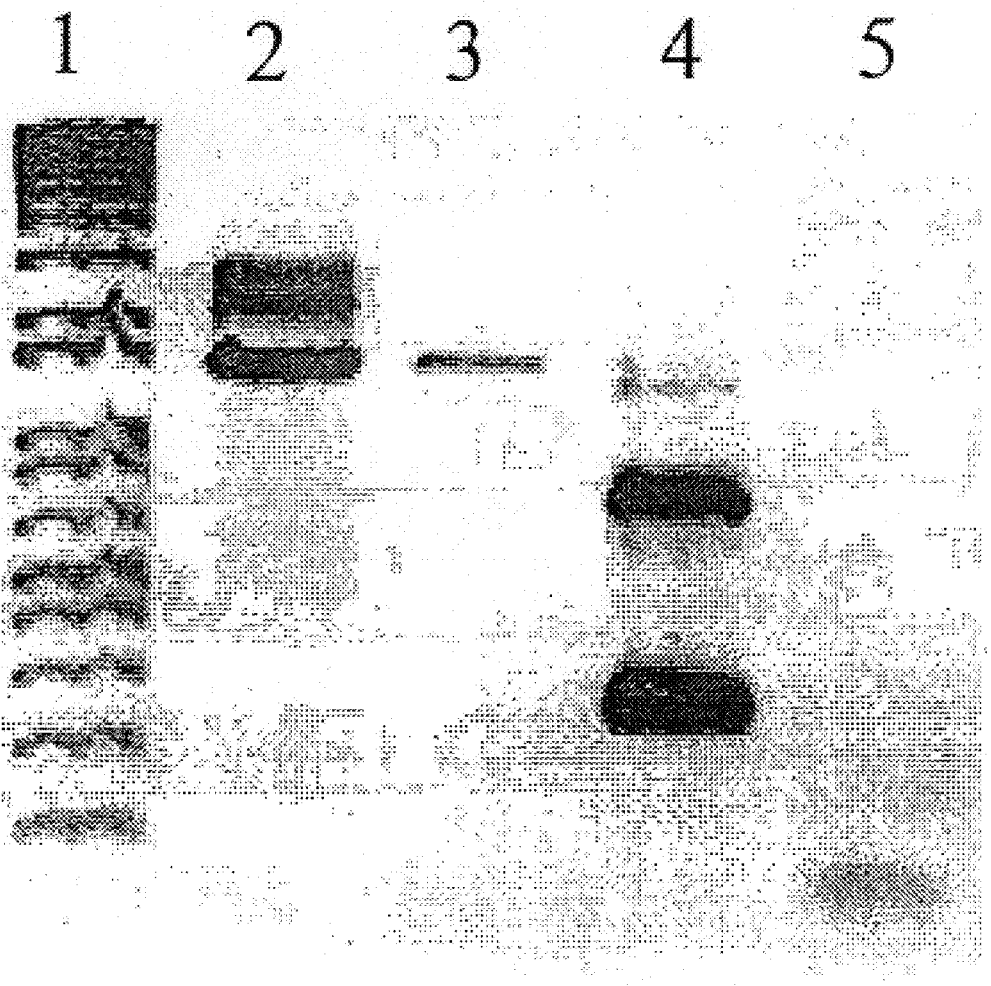
FIG. 4 is a photograph of an electrophoresis gel showing the PCR reactions obtained by using various concentrations of (1) the universal and competitor primers or (2) the universal, competitive, and terminator primers.

PCRs shown in FIG. 4

| lane | template | primers |
|---|---|---|
| 1 | 1 KB PLUS Marker (Gibco-BRL) | |
| 2 | *E. coli* genomic DNA 100 ng | 200 nM U |
| 3 | *E. coli* genomic DNA 100 ng | 200 nM U, 200 nM T |
| 4 | *E. coli* genomic DNA 100 ng | 200 nM U, 200 nM C |
| 5 | *E. coli* genomic DNA 100 ng | 200 nM U, 200 nM T, 200 nM C |

The addition of the terminator oligo set partially inhibited the generation of the *E. coli*-specific PCR product at a concentration of 100 nM (FIG. 4, lane 3). At higher concentrations of terminator oligos, the generation of an *E. coli*-specific PCR product was completely inhibited (data not shown). As was seen before, the competitor primer set also inhibited the generation of a full-length PCR product, while producing large amounts of smaller, *E. coli*-specific PCR products (FIG. 4, lane 4). Most importantly, the combination of competitor and terminator primer sets resulted in the complete elimination of the full-length *E. coli*-specific PCR product without the production of smaller, *E. coli*-specific PCR products (lane 5). Therefore, a synergy exists with the use of the competitor primer and terminator oligo sets: in combination they inhibit the PCR amplification of a specific undesired template or small fragments thereof.

PCR optimization:

Once it was discovered that the terminal primer modifications effective at inhibiting the PCR amplification of a specific DNA template, it was necessary to investigate the influence of several variables on this template-specific inhibition. The PCR can be optimized for the following parameters: the optimal amount of each primer set, the optimal amount of polymerase, the optimal amount of template, and the optimal annealing temperature. PCR conditions are optimized to inhibit the amplification of undesired DNA template and to promote the amplification of the desired DNA template. So that all the desired DNA template is amplified, the PCR is preferably optimized to err on the side of amplifying all desired DNA templates while permitting some amplification of undesired DNA template, i. e., to err on the side of being inclusive, not exclusive. This prevents the loss of PCR products from the desired DNA template. This may result in some undesired DNA template being present in the final amplification product. However, the amount of the undesired DNA template is diminished compared to PCR amplification in the absence of terminator oligos.

To optimize the amount of each primer, the primers and template are individually diluted and then added to the PCR reaction. The primers and template are preferably serially diluted.

The optimal amount of polymerase is determined by adding various amounts of the polymerase to duplicate PCR reactions, running the PCR, and visualizing the PCR products after electrophoresing them on a gel. For example, 0.5 U, 1.0 U, 1.5 U, 2.0 U. and 2.5 U of Taq DNA polymerase can be added to duplicate PCR reactions. The optimal amount of polymerase typically is the amount that produces the strongest desired PCR product without producing undesired PCR products. It was found that at least 2.5 U of Taq polymerase per 100 µl reaction were necessary for optimal production of the desired PCR products (data not shown).

The optimal annealing temperature is determined by setting up duplicate PCR reactions and running them using different annealing temperatures in the PCR reaction. For example, annealing temperatures of 66° C., 62° C., 58° C., 54° C., 50° C., and 46° C. are tested. As is well-known in the relevant art, the optimal annealing temperature depends on the $T_m$ of the primer used in the PCR. In short, for a given length primer, the higher the GC content of that primer, the higher the optimal annealing temperature will be. Similarly, the longer the length of a primer, the higher the optimal annealing temperature will be. The optimal annealing temperature for the inhibition of PCR amplification of the E. coli 16S rRNA gene was determined by conducting the PCR in a temperature gradient thermocycler (Stratagene, Inc., La Jolla, Calif.) which revealed that an annealing temperature of 58° C. provided the maximum degree of template-specific inhibition (data not shown).

The following examples are included herein solely to aid in a more complete understanding of the invention disclosed and claimed herein. The Examples do not limit the scope of the invention in any fashion.

EXAMPLES

To exemplify the invention, the 16S rRNA gene of E. coli was chosen for inhibition, allowing heterogeneous 16S rRNA genes from diverse bacteria to be PCR amplified. The following PCR conditions result in the selective amplification of non-E. coli 16S rRNA genes: one minute denaturation at 94° C., followed by 40 cycles in a thermocycler (preferably a Robocycler 96 by Stratagene) consisting of 30 sec at 94° C., 90 sec at 58° C., 150 sec at 72° C., and then 5 minutes extension at 72° C. Optimal primer concentrations were found to be 200 nM for each universal primer, 100 nM for each terminator primer, and 50 nM for each competitor primer. These conditions can be applied to a wide variety of PCR applications in which one or more DNA template needs to be inhibited.

Example 1

PCR Amplification of the Bacillus cereus 16S rRNA Gene

The ultimate goal of this project was to PCR amplify the non-host 16S rRNA genes from a genomic DNA library constructed from soil DNA. Prior to using template-specific inhibition in a PCR on this soil genomic library, this technology was tested on a genomic library constructed from a soil bacterium, B. cereus. This collection of genomic DNA fragments isolated from B. cereus represents every gene of this organism, with each clone contained within an E. coli host cell having an average size of 98 kilobases. Because the sequence of the B. cereus 16S rRNA gene is known, primers were designed to specifically amplify this gene, revealing that several clones from the B. cereus library possessed the B. cereus 16S rRNA gene (data not shown). Control PCR amplifications using the B. cereus-specific primers with E. coli genomic DNA did not produce a PCR product (data not shown). Therefore, a system was created to test the ability of template-specific inhibition in a PCR to amplify selectively the non-E. coli 16S rRNA genes in a genomic library, under conditions where such a gene was known to exist.

In order to screen large numbers of clones for the gene of interest (e.g., 16S rRNA gene), clones by necessity have to be pooled together. This raises a critical question as to the concentration of pooled clone DNA that can be added to a PCR for the selective amplification of a non-host DNA template. For this experiment, the B. cereus 16S rRNA gene-containing Plate #3 was used as the positive control, the E. coli genomic DNA was used as the negative control, testing 1 ng, 10 ng, and 100 ng of added DNA template in the PCR. Additionally, concentrations of 0, 10 nM, and 100 mM of the competitor and terminator primer sets were used. The PCRs were set up as shown in Table 3 and the reaction products loaded into the lanes of the gel shown in FIG. 5.

TABLE 3

Figure 5:
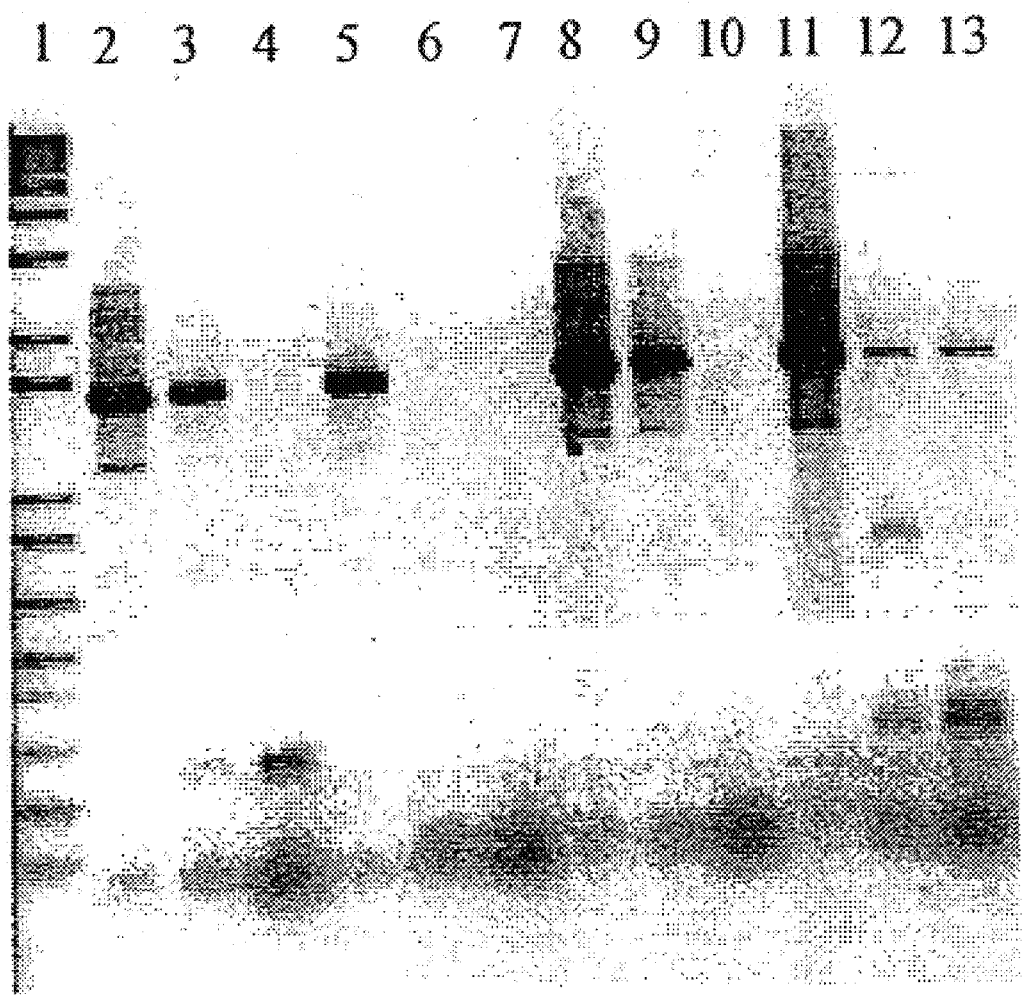
FIG. 5 is a photograph of an electrophoresis gel depicting a PCR run to optimize the concentration of the universal, competitor, and terminator primer sets.

PCRs shown in FIG. 5

| lane | template | primers |
|---|---|---|
| 1 | 1 KB PLUS Marker (Gibco-BRL) | |
| 2 | E. coli 100 ng | U |
| 3 | E. coli 100 ng | U, 1 µM C, T |
| 4 | E. coli 100 ng | U, 10 µM C, T |
| 5 | UW 85 #3 1 ng | U |
| 6 | UW 85 #3 1 ng | U, 1 µM C, T |
| 7 | UW 85 #3 1 ng | U, 10 µM C, T |
| 8 | UW 85 #3 10 ng | U |
| 9 | UW 85 #3 10 ng | U, |

TABLE 3-continued

PCRs shown in FIG. 5

| lane | template | primers |
|---|---|---|
| 10 | UW 85 #3 10 ng | 1 μM C, T<br>U,<br>10 μM C, T |
| 11 | UW 85 #3 100 ng | U |
| 12 | UW 85 #3 100 ng | U,<br>1 μM C, T |
| 13 | UW 85 #3 100 ng | U,<br>10 μM C, T |

Many of these combinations generated full-length 1.5 kb PCR products (see lanes 2, 3, 5, 8, 9, and 11–13 of FIG. 5). However, because the UW85 clones (in lanes 5, 8, 9, and 11–13) were a *B. cereus* library in *E. coli*, from which the 16S genes can be amplified from both the *B. cereus* and *E. coli*, the source of these PCR products was not known. That is, whether *E. coli* or non-*E. coli* genes (or both) amplified was not known.

Figure 6:
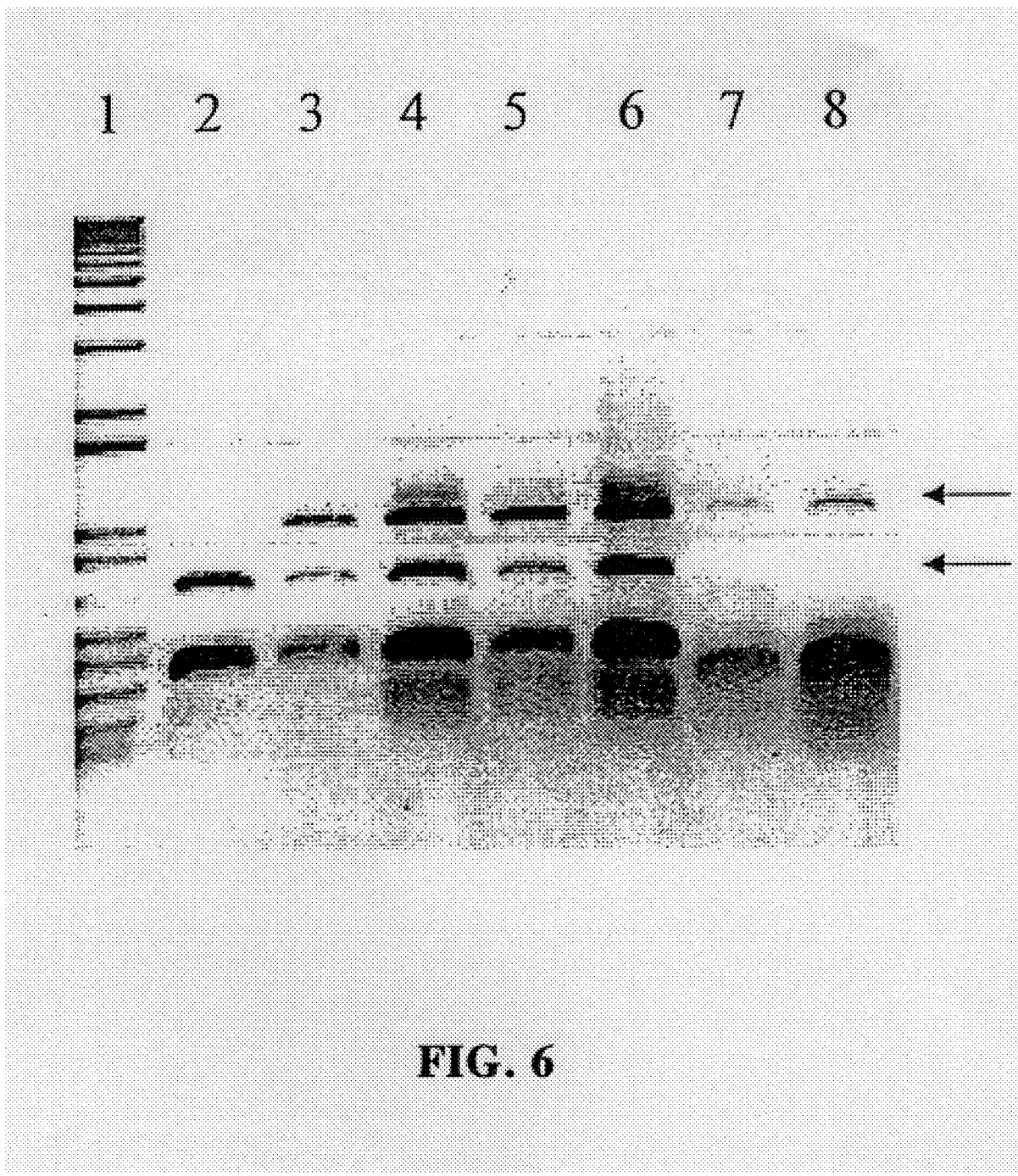
FIG. 6 is a photograph of an electrophoresis gel depicting a restriction digestion of the PCR products of FIG. 5 to differentiate *E. coli*-derived PCR products from *B. cereus*-derived PCR products.

To determine this, a restriction digest was performed on the PCR products so that different sized fragments of DNA were generated from templates of different origin. Amplified rDNA restriction analysis (ARDRA) was used to differentiate the PCR products generated from multiple organisms into a unique pattern of bands. Specifically, HinF I, which differentiates *E. coli* and *B. cereus*, was used. FIG. 6 shows the restriction digestions of the PCR products of FIG. 5. The lanes are FIG. 6 are described in Table 4:

TABLE 4

PCRs shown in FIG. 6

| lane | template | primer set |
|---|---|---|
| 1 | 1 KB PLUS Marker<br>(Gibco-BRL) | |
| 2 | *E. coli* control | U |
| 3 | UW85 (#3) 1 ng | U |
| 4 | UW85 (#3) 10 ng | U |
| 5 | UW85 (#3) 10 ng | U, and 1 μM C and T |
| 6 | UW85 (#3) 100 ng | U |
| 7 | UW85 (#3) 100 ng | U, and 1 μM C and T |
| 8 | UW85 (#3) 100 ng | U, and 10 μM C and T |

The top arrow in FIG. 6 denotes a *B. cereus*-specific band. The bottom arrow denotes an *E. coli*-specific band. From these digests, it was determined that the optimal conditions for selectively amplifying non-*E. coli* 16S genes from a complex mixture of templates is a template concentration of 100 ng per reaction, and a 100 nM final concentration of each of the competitor and terminator primer set.

Figure 7:
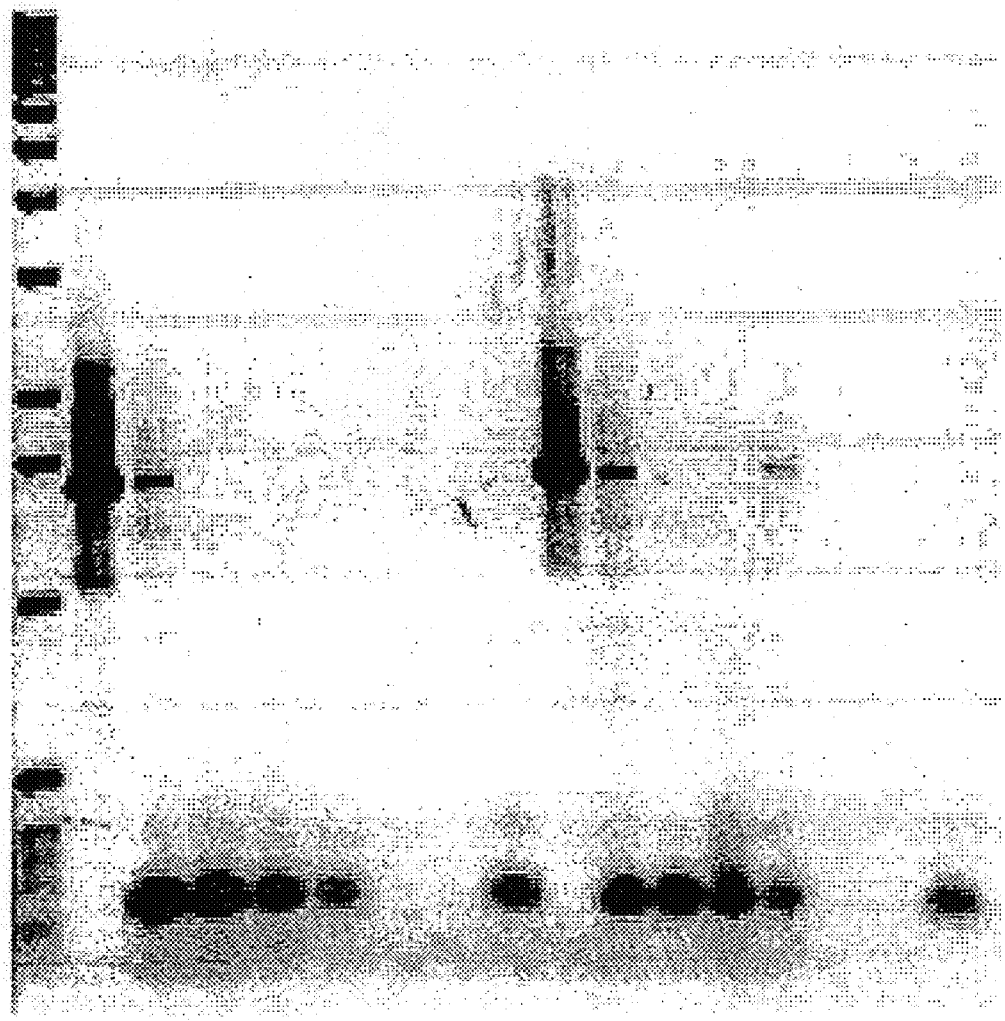
FIG. 7 is a photograph of an electrophoresis gel depicting a PCR run to optimize the ratio of the competitor primer set to the terminator primer set in the subject invention.

Next the optimal ratio of competitor to terminator primer sets was determined (see FIG. 7). Forty cycles of PCR were carried out using an annealing temperature of 58° C. One set of reactions (lanes 2–9) used 100 ng of *E. coli* as the template. A second set (lanes 10–17) used 100 ng of P67, a pooled population known to have a 16S-containing clone. All PCR reactions included the universal (U) primer set at 200 nM. The competitor (C) and terminator (T) primer concentrations are described in Table 5. Some reactions had only the forward (F) primer or the reverse (R) primer. If this is not indicated, then the full primer set was used. The lanes (except for the molecular weight marker in lane 1) were as described in Table 5:

TABLE 5

PCRs shown in FIG. 7

| lane | temp. | primer[1] |
|---|---|---|
| 2 | *E. coli* | |
| 3 | *E. coli* | 100 nM C, and 100 nM T |
| 4 | *E. coli* | 100 nM C and 50 nM T |
| 5 | *E. coli* | 100 nM C and 10 nM T |
| 6 | *E. coli* | 50 nM C and 100 nM T |
| 7 | *E. coli* | 10 nM C and 100 nM T |
| 8 | *E. coli* | 100 nM C (F only) and<br>100 nM T (R only) |
| 9 | *E. coli* | 100 nM C (R only)<br>and 100 nM T (F only) |

| lane | temp. | primer |
|---|---|---|
| 10 | P67 | |
| 11 | P67 | 100 nM C, and 100 nM T |
| 12 | P67 | 100 nM C and 50 nM T |
| 13 | P67 | 100 nM C and 10 nM T |
| 14 | P67 | 50 nM C and 100 nM T |
| 15 | P67 | 10 nM C and 100 nM T |
| 16 | P67 | 100 nM C (F only) and<br>100 nM T (R only) |
| 17 | P67 | 100 nM C (R only)<br>and 100 nM T (F only) |

[1]primers in addition to 200 nM universal primer

A faint band can be seen in lane 13, which is a band produced from the pooled population know to have a 16S-containing clone. These same conditions do not produce a PCR product from *E. coli* (lane 5). Based on this, the following primer concentrations were preferred: 200 nM universal primer, 100 nM terminator primer, 50 nM competitor primer, and about 100 ng template DNA.

Example 2

PCR Amplification of 16S rRNA Genes From a Soil Genomic Library

Figure 8:
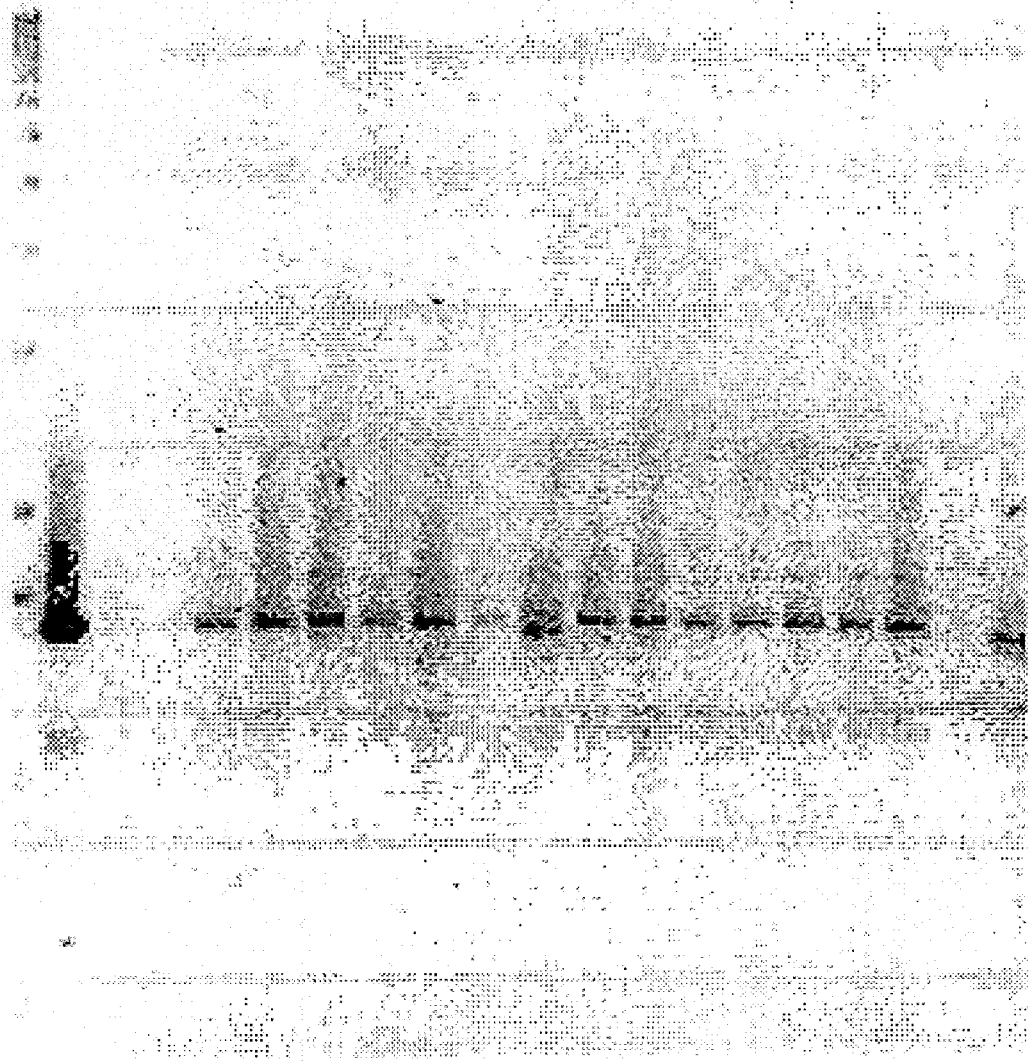
FIG. 8 is a photograph of an electrophoresis gel depicting the use of the subject method on a 16S genomic library in *E. coli*.

Once the key variables for selectively amplifying the non-host 16S rRNA genes from a pooled genomic library had been determined (i.e., 100 ng pooled clone DNA), these conditions were applied to pooled plates representing 48 distinct clones from a soil genomic library (disclosed as SL1 in copending patent application by Goodman, Handelsman, Rondon, and Bettermann) were screened for the presence of 16S rRNA genes. Because the library was constructed using genomic DNA from soil microbes, each clone potentially contained a 16S rRNA gene from a soil microbe. Based upon the anticipated frequency of the 16S rRNA genes in the soil genomic library, it was expected that approximately 10–20% of the pooled clones (i.e., 48 clones per pool) would contain a single clone with a 16S rRNA gene. Thus, the BAC clones included the host *E. coli* 16S genes and possibly 16S rRNA genes from a soil microbe. Referring to FIG. 8, the lanes of the gel contained the following samples as shown in Table 6:

TABLE 6

PCRs shown in FIG. 8

| lane | template | primers |
|---|---|---|
| 1 | 1 KB PLUS Marker<br>(Gibco-BRL) | |
| 2 | *E. coli* | U |
| 3 | *E. coli* | U, C, T |
| 4 | P56 | U, C, T |

TABLE 6-continued

PCRs shown in FIG. 8

| lane | template | primers |
|------|----------|---------|
| 5    | P57      | U, C, T |
| 6    | P58      | U, C, T |
| 7    | P59      | U, C, T |
| 8    | P60      | U, C, T |
| 9    | P61      | U, C, T |
| 10   | P62      | U, C, T |
| 11   | P63      | U, C, T |
| 12   | P64      | U, C, T |
| 13   | P65      | U, C, T |
| 14   | P66      | U, C, T |
| 15   | P67      | U, C, T |
| 16   | P68      | U, C, T |
| 17   | P69      | U, C, T |
| 18   | P70      | U, C, T |
| 19   | P71      | U, C, T |
| 20   | P72      | U, C, T |

As FIG. 8 shows, PCRs produced the 1.5 kb full-length PCR product for all reactions except the ones in lane 2 (because the competitor and terminator primers inhibited the amplification of the E. coli 16S gene). The PCR products of lane 3, 9, and 18 were weak.

Figure 9:
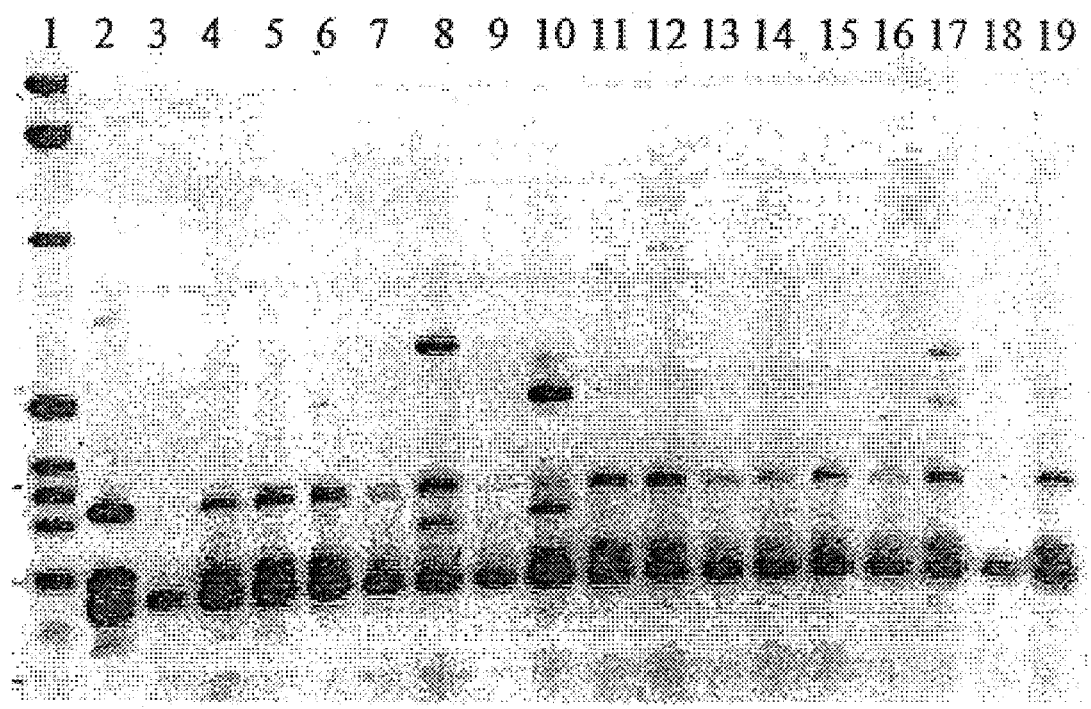
FIG. 9 is a photograph of an electrophoresis gel depicting the restriction digestion of the PCR products of FIG. 8 to differentiate *E. coli*-derived PCR products from non-*E. coli*-derived PCR products.

Because the PCR products from the clones could be due to the amplification of both the E. coli 16S gene and a cloned 16S gene, the PCR products shown in FIG. 8 were cut with restriction enzymes using the ARDRA technique described above. The resulting restriction fragments are shown in FIG. 9 (note that samples in FIG. 9 are identical to those in FIG. 8 except that the E. coli genomic control with the T and C primer (lane 3 of FIG. 8) is absent). The restriction fragments from the amplified E. coli (shown in lane 2 of FIG. 9) were compared to the restriction fragments in other lanes. As FIG. 9 shows, several different restriction bands appeared in the cloned DNA samples when compared to the E. coli control reaction of lane 2 (see lanes 8 (P61) 10 (P63), and 17 (P70) of FIG. 9). The 16S genes from the positive pooled populations were cloned and sequenced, revealing the origin of the BAC clones that contained the 16S genes.

The invention is not limited to the particular reagents, protocols, etc. described hereinabove, but includes all modified and equivalent forms thereof which are within the scope of the following claims.

What is claimed is:

1. A method for selectively amplifying a desired nucleic acid, comprising:
   (a) providing a first primer set that binds to both the desired nucleic acid and undesired nucleic acid present in a sample of nucleic acid to be amplified;
   (b) providing a second primer set that binds to the undesired nucleic acid, wherein the second primer set inhibits the amplification of the undesired nucleic acid by the first primer set;
   (c) providing a third primer set that binds to the undesired nucleic acid, wherein, when compared to the second set, the third primer set further inhibits the amplification of the undesired nucleic acid by the first primer set; and
   (d) amplifying the desired nucleic acid with the first primer set.

2. The method of claim 1, wherein in step (a) a first primer set is provided comprising a forward primer and a reverse primer, and in step (b) a second primer set is provided comprising a forward primer and a reverse primer, wherein the forward primer of both the first and second primer sets binds to the same strand of the undesired nucleic acid, and the reverse primer of both the first and second primer sets that binds to the same strand of the undesired nucleic acid.

3. The method of claim 2, wherein in step (c) a third primer set is provided comprising a forward primer and a reverse primer, wherein the forward primer and reverse primers of the third primer set are each modified at their 3' termini.

4. The method of claim 3, wherein the forward and reverse primers of the third primer set are each modified to contain a group that at least partially inhibits primer extension.

5. The method of claim 4, wherein the modification comprises a phosphoramidite.

6. The method of claim 5, wherein the phosphoramidite is selected from the group consisting of 3-(4,4'-dimethoxyltrityloxy)propyl-1-{(2-cyanoethyl)-(N,N-diisopropyl)}-phosphoramidite, 2-{2-(4,4'-dimethoxytrityloxy)-ethylsulfonyl}ethyl-(2-cyanoethyl)-(N,N,-diisopropyl)-phosphoramidite), 3-{ (4,4' - Dimethoxytrityloxy)-2,2-dicarboxyethyl}propyl-(2-cyanoethyl)-(N,N-di isopropyl)-phosphoramidite, and support-bound phosphoramidites.

7. The method of claim 3, wherein the forward and reverse primers of the third set are each modified to contain a base that prevents primer extension.

8. The method of claim 3, wherein the modification comprises a phosphate group or a phosphate ester.

9. The method of claim 3, wherein the modification comprises an inverted 3'-3' linkage at the 3' hydroxyl group of the primer or a 2',3' dideoxynucleoside support.

10. The method of claim 3, wherein the modification comprises a 3'-deoxynucleoside support.

11. The method of claim 1, wherein in step (a) a first primer set is provided that binds to 16S rRNA genes of the desired DNA template and the undesired DNA template.

12. The method of claim 1, wherein in step (d) the desired nucleic acid is amplified with a polymerase chain reaction.

13. The method of claim 1, wherein the desired nucleic acid comprises a desired DNA template, and the undesired nucleic acid comprises an undesired DNA template.

14. The method of claim 1, wherein in step (c) the third primer set comprises a forward primer and a reverse primer, wherein the forward primer of the third primer set binds to the opposite strand of the undesired nucleic acid as the forward primers of the first and second primer sets, and the reverse primer of the third primer set binds to the opposite strand of the undesired nucleic acid as the reverse primer of the universal and competitor primer sets.

15. The method of claim 14, wherein the forward primer and reverse primer of the third primer set are each modified at their 3' and 5' termini.

16. The method of claim 15, wherein the 5' modification increases primer-DNA affinity and prevents displacement of the third primer set.

17. The method of claim 16, wherein the 5' modification comprises an intercalating molecule.

18. The method of claim 17, wherein the intercalating molecule comprises acridine orange.

19. The method of claim 16, wherein the 5' modification comprises a non-intercalating molecule.

20. The method of claim 19, wherein the non-intercalating molecule comprises biotin.

21. The method of claim 15, wherein the 3' modification prevents primer extension.

22. A method for selectively amplifying a desired nucleic acid, comprising:
  (a) providing a first primer set that binds to both a desired nucleic acid and an undesired nucleic acid present in a sample of nucleic acid to be amplified, wherein the first primer set comprises a forward primer and a reverse primer;
  (b) providing a second primer set that binds to the undesired nucleic acid, wherein
    (i) the second primer set at least partially inhibits the amplification of the undesired nucleic acid by the first primer set, wherein the second primer set comprises a forward primer and a reverse primer, and
    (ii) the forward primer of both the first and second primer sets binds to the same strand of the undesired nucleic acid, and the reverse primer of both the first and second primer sets binds to the same strand of the undesired nucleic acid,
  (c) providing a third primer set that blocks the amplification of the undesired nucleic acid with the first primer set, wherein
    (i) the third primer set comprises a forward primer and a reverse primer,
    (ii) the third primer set binds to the undesired nucleic acid and at least partially inhibits the amplification of the undesired nucleic acid by the first primer set,
    (iii) the forward primer of the third primer set binds to the opposite strand of the undesired nucleic acid as the forward primers of the universal and competitor primer sets, and the reverse primer of the third primer set binds to the opposite strand of the undesired nucleic acid as the reverse primer of the universal and competitor primer sets,
    (iv) the forward primer and reverse primer of the third primer set are each modified at their 3' and 5' termini,
    (v) the 5' modification increases primer-DNA affinity and prevents displacement of the third primer set, and
    (vi) the 3' modification prevents primer extension; and
  (d) amplifying the desired nucleic acid with the first primer set, wherein the desired nucleic acid is amplified with a polymerase chain reaction.

* * * * *

SEQUENCE LISTING

<160> NUMBER OF SEQ ID NOS: 6

<210> SEQ ID NO: 1
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 1
gatgtcgact tggaggttgt gccc                                            24

<210> SEQ ID NO: 2
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 2
ccgatggcaa gaggcccgaa ggtccccc                                        28

<210> SEQ ID NO: 3
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 3
agagtttgat cmtggctcag                                                 20

```
<210> SEQ ID NO: 4
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 4
ggytaccttg ttacgactt                                                  19

<210> SEQ ID NO: 5
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 5
gggggacctt cgggcctctt gccatcgg                                        28

<210> SEQ ID NO: 6
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 6
gggcacaacc tccaagtcga catc                                            24
```